(12) United States Patent
Becker

(10) Patent No.: US 11,791,039 B2
(45) Date of Patent: Oct. 17, 2023

(54) SYSTEM FOR COMMUNICATION OF DATA

(71) Applicant: Stryker Corporation, Kalamazoo, MI (US)

(72) Inventor: David Becker, Grand Rapids, MI (US)

(73) Assignee: Stryker Corporation, Kalamazoo, MI (US)

( * ) Notice: Subject to any disclaimer, the term of this patent is extended or adjusted under 35 U.S.C. 154(b) by 635 days.

(21) Appl. No.: 16/729,609

(22) Filed: Dec. 30, 2019

(65) Prior Publication Data

US 2020/0135333 A1 Apr. 30, 2020

Related U.S. Application Data

(63) Continuation of application No. PCT/US2018/040595, filed on Jul. 2, 2018.
(Continued)

(51) Int. Cl.
*G16H 40/40* (2018.01)
*G16H 40/60* (2018.01)
(Continued)

(52) U.S. Cl.
CPC ............ *G16H 40/40* (2018.01); *G16H 40/60* (2018.01); *H04L 65/1036* (2013.01); *H04L 67/303* (2013.01); *H04L 69/08* (2013.01)

(58) Field of Classification Search
CPC .. G16H 40/40; G16H 40/60; H04L 29/06258; H04L 67/303; H04L 69/08
See application file for complete search history.

(56) References Cited

U.S. PATENT DOCUMENTS

| 7,690,059 B2 | 4/2010 | Lemire et al. |
| 7,774,211 B1 | 8/2010 | Mullen et al. |

(Continued)

FOREIGN PATENT DOCUMENTS

| WO | 2012033947 A2 | 3/2012 |
| WO | 2013109517 A1 | 7/2013 |

(Continued)

OTHER PUBLICATIONS

Jennifer Bresnick, How Fog Computing May Power the Healthcare Internet of Things, Health IT Analytics (Aug. 23, 2016) (Year: 2016).*

(Continued)

*Primary Examiner* — Evangeline Barr
*Assistant Examiner* — Jordan L Jackson
(74) *Attorney, Agent, or Firm* — Howard & Howard Attorneys PLLC

(57) ABSTRACT

A system for communication of data is provided. The system includes a medical device. A data consuming device is positioned at a first network layer. An edge communication device is positioned at a second network layer. The edge communication device is in communication with the medical device to receive data from the medical device. The edge communication device has a profile. The profile defines a data format for the data and a communication path for transmitting the data between the network layers. A gateway device is configured to route the data from the edge communication device to the data consuming device via the communication path. The edge communication device is also configured to modify the data format to correspond to the data consuming device and to format the data according to the data format.

20 Claims, 8 Drawing Sheets

Related U.S. Application Data

(60) Provisional application No. 62/528,192, filed on Jul. 3, 2017.

(51) Int. Cl.
*H04L 67/303* (2022.01)
*H04L 69/08* (2022.01)
*H04L 65/1033* (2022.01)

(56) References Cited

U.S. PATENT DOCUMENTS

| | | | |
|---|---|---|---|
| 8,102,254 | B2 | 1/2012 | Becker et al. |
| 8,126,729 | B2* | 2/2012 | Dicks ............ G16H 40/67 |
| | | | 710/16 |
| 9,833,194 | B2 | 12/2017 | Hayes et al. |
| 9,902,762 | B2 | 2/2018 | Camphausen et al. |
| 10,200,241 | B2 | 2/2019 | Shen et al. |
| 10,319,056 | B1* | 6/2019 | Perez ............ G06Q 50/30 |
| 10,693,966 | B2* | 6/2020 | Becker ............ G08G 1/04 |
| 2002/0193969 | A1 | 12/2002 | Frantz et al. |
| 2005/0187529 | A1 | 8/2005 | Reasoner et al. |
| 2007/0163045 | A1 | 7/2007 | Becker et al. |
| 2008/0151932 | A1* | 6/2008 | Wormer ............ G06F 9/54 |
| | | | 370/466 |
| 2009/0063187 | A1* | 3/2009 | Johnson ............ H04L 67/30 |
| | | | 705/2 |
| 2010/0250697 | A1* | 9/2010 | Hansen ............ A61B 5/157 |
| | | | 709/208 |
| 2011/0093285 | A1* | 4/2011 | Dicks ............ G16H 40/63 |
| | | | 709/217 |
| 2013/0032479 | A1 | 2/2013 | Hanko et al. |
| 2013/0190674 | A1* | 7/2013 | Case ............ G16H 40/63 |
| | | | 604/6.01 |
| 2014/0077956 | A1 | 3/2014 | Sampath et al. |
| 2014/0152466 | A1 | 6/2014 | Wiesner et al. |
| 2014/0343639 | A1 | 11/2014 | Hopper et al. |
| 2015/0206408 | A1* | 7/2015 | LaLonde ............ A61B 5/349 |
| | | | 340/539.12 |
| 2016/0127514 | A1* | 5/2016 | Maksumov ......... H04L 41/0226 |
| | | | 709/202 |
| 2017/0147761 | A1* | 5/2017 | Moskal ............ G16H 70/60 |
| 2019/0244707 | A1 | 8/2019 | Becker et al. |

FOREIGN PATENT DOCUMENTS

| | | |
|---|---|---|
| WO | 2018013666 A1 | 1/2018 |
| WO | 2019010127 A1 | 1/2019 |

OTHER PUBLICATIONS

Gia et al., Fog Computing in Healthcare Internet of Things: A Case Study on ECG Feature Extraction, 2015 IEEE International Conference on Computer and Information Technology; 356-36 (Year: 2015).*

International Search Report for Application No. PCT/US2017/041681 dated Oct. 18, 2017, 4 pages.

International Search Report for Application No. PCT/US2018/040595 dated Oct. 11, 2018, 4 pages.

* cited by examiner

SYSTEM FOR COMMUNICATION OF DATA

CROSS REFERENCE TO RELATED APPLICATIONS

This application is a continuation application of International Application No. PCT/US2018/040595, filed Jul. 2, 2018, which claims priority to U.S. Provisional Application 62/528,192, filed Jul. 3, 2017, the disclosures of which are incorporated herein by reference in their entirety.

SUGGESTED CLASSIFICATION

G16H 80/00: Healthcare Informatics, i.e., information and communication technology specially adapted for facilitating communication between medical practitioners or patients, e.g. for collaborative diagnosis, therapy or health monitoring.

The subject disclosure relates to a system for communication of medical data within a network in a surgical or medical environment, and more specifically, a system that includes an edge communication device having a profile for facilitating the communication of medical data.

DESCRIPTION OF RELATED ART

A wide variety of medical devices may be used in a hospital or other health care setting, including handheld surgical tools, hospital beds, endoscopes, surgical navigation devices, and patient monitoring devices, for example. These devices may gather a variety of information during use. For example, a handheld surgical tool may store tool diagnostic information, tool usage information, and tool identification information within a memory internal to the tool. Different tools may store different types of information in different formats and may need to transmit these different types of information to one or more other devices on a network, including operating room computers, central hospital servers, and off-site databases, such as cloud storage databases. Furthermore, each of these devices may understand different data formats and protocols, and use different types of wired or wireless communication technologies. Each of the devices may use multiple types of wired or wireless communication technologies either separately or simultaneously.

In addition, medical devices or other devices used within a healthcare setting may be initially certified and placed in the field based on the functions and services available to the devices at the time. If new services or functionality are desired to be added to the devices at a later time, software on the devices may need to be updated and the devices may need to be re-certified. This can cause additional expense and downtime for the devices and for the hospitals or other health care facilities that use the devices.

SUMMARY

One embodiment of a system for data communication of data is provided. The system includes a medical device comprising a primary processor configured to perform operational functions, a primary memory device programmed for performing operational functions, a first circuit board, one of the primary processor and primary memory device being mounted to the first circuit board. The system further includes an edge communication device comprising a secondary memory device, a transceiver configured to communicate with at least one data consuming device, a second circuit board, the secondary memory device and the transceiver mounted to the second circuit board, wherein the first circuit board is isolated from the second circuit board such that the secondary memory device is updateable without impacting regulated functions of the medical device, and a plurality of adapters configured to enable data communication between the transceiver and the at least one data consuming device. The edge communication device is configured to select at least one adapter from the plurality of adapters to exchange data regarding the medical device with the at least one data consuming device. The system further includes a housing configured to encase the medical device and the edge communication device.

Another embodiment for data communication is provided. The system includes a medical device and a data consuming device, and an edge communication device positioned at a second network layer and configured to communicate with the medical device, the edge communication device having a profile defining a communication path for transmitting data between the first and second network layers. The system further includes a gateway device configured to route data from the edge communication device to the data consuming device via the communication path.

In yet another embodiment, a system for communication of data is provided. The system includes a medical device; at least one data consuming device; an edge communication device including a memory and a plurality of adaptors, said edge communication device being in communication with said medical device and each of said adaptors being configured to enable data communication with said at least one data consuming device via one or more of a plurality of protocols. The system further includes a profile stored in said memory, said profile being at least partially writable by a device remote from said edge communication device and said profile configuring said edge communication device to select one of said adaptors to enable data communication with said at least one data consuming device.

BRIEF DESCRIPTION OF THE DRAWINGS

Advantages of the present disclosure will be readily appreciated, as the same becomes better understood by reference to the following detailed description, when considered in connection with the accompanying drawings.

DETAILED DESCRIPTION

Referring to the Figures, wherein like numerals indicate like or corresponding parts throughout several views, aspects of a system 10 for communication of data are provided.

Figure 1:
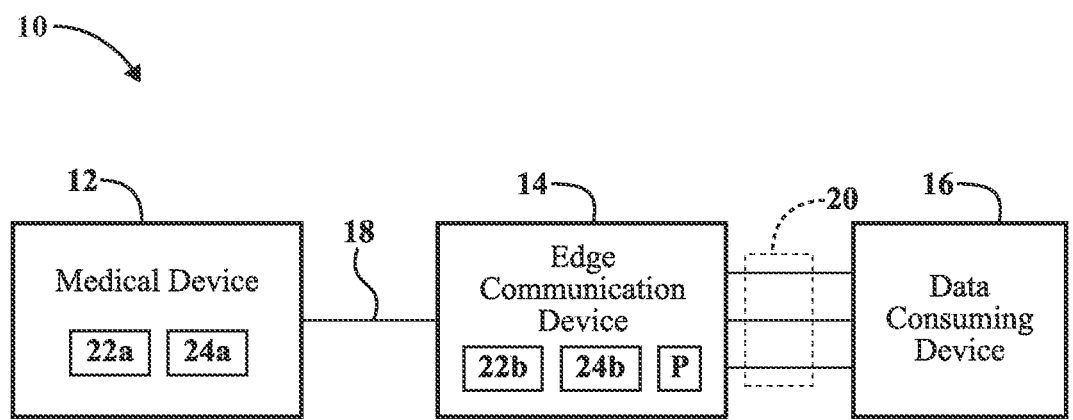
FIG. 1 is a block diagram of a system for communication of data including a medical device in communication with an edge communication device.

FIG. 1 is a block diagram illustrating the system 10 including a medical device 12, an edge communication device 14, and a data consuming device 16. The medical device 12 is in communication with the edge communication device 14 via a data connection 18. The data connection 18 may be wired or wireless. The data connection 18 enables the medical device 12 to transmit data to the edge communication device 14, and in some embodiments, to receive data from the edge communication device 14. While the embodiments are generally described herein as including a medical device 12 in communication with an associated edge communication device 14, it should be recognized that other devices may incorporate or be in communication with an associated edge communication device 14, such as one or more gateway devices or other devices within a network hierarchy.

It should be appreciated that while a single edge communication device 14, a single medical device 12, and a single data consuming device 16 are illustrated herein, the system 10 may include any number of edge communication devices 14, medical devices 12, and data consuming devices 16. The edge communication device 14 is configured to receive data from the medical device 12 via the data connection 18 and to transmit the data through one or more networks, such as one or more networks of a network hierarchy 62 (shown in FIG. 7). In one embodiment, the medical device 12 is only connected to the network through the edge communication device 14. In other embodiments, the medical device 12 may be connected to the edge communication device 14 and/or other devices through the network. For example, the medical device 12 may be a surgical tool usable in a surgical operation. The surgical tool may include a plurality of sensors that gather information during the surgical procedure. The surgical tool may transmit information from the sensors gathered during the surgical procedure to the edge communication device 14, and the edge communication device 14 may transmit data containing the information gathered during the surgical procedure to other devices in the network or to other devices in other layers of the network hierarchy 62.

The medical device 12 may be any type of medical device 12 capable of gathering data. For example, the medical device 12 may be, without limitation, a surgical tool, a hospital bed, an endoscope, a console. Any of these medical devices may be further configured to accept data from hospital personnel. The medical device 12 may have one or more sensors for gathering sensor data, patient data, image data, device usage data, or any other type of data. In some embodiments, the medical device 12 may comprise Class II or Class III medical devices such as classified by the Food and Drug Administration (FDA).

Class II medical devices are devices where General Controls are not sufficient to assure safety and effectiveness and existing methods/standards/guidance documents are available to provide assurances of safety and effectiveness. In addition to compliance with General Controls, Class II devices are required to comply with Special Controls. Special Controls may include: special labelling requirements, mandatory performance standards, both International and United States; postmarket surveillance; and/or FDA medical device specific guidance.

Class II devices typically require pre-market notification by submission and FDA review of a 510(k) clearance to market submission. Examples of Class II devices include biological indicators, x-ray systems, gas analyzers, pumps, and surgical drapes. Class III medical devices have the most stringent regulatory controls. For Class III medical devices, sufficient information is not available to assure safety and effectiveness through the application of General Controls and Special Controls. Class III devices usually support or sustain human life, are of substantial importance in preventing impairment of human health, or present a potential unreasonable risk of illness or injury to the patient. Typically, a Pre-Market Approval (PMA) submission to the FDA is required to allow marketing of a Class III medical device. Examples of Class III devices that require a PMA are: replacement heart valves, silicone gel-filled breast implants, and implanted cerebella stimulators.

The medical device 12 includes a processor 22 and a memory 24, such as processor 22*a* and memory 24*a*. The processor 22 is configured to execute computer-executable instructions perform the functions of the edge communication device 14. The processor 22 may be a microprocessor, a microcontroller, a field programmable gate array (FPGA), a system on a chip (SoC), or any other suitable type of processor for executing the functions. In some embodiments, the processor 22 may be implemented on a chip such as an integrated circuit (IC), a printed circuit board (PCB), or the like. The memory 24 is configured to store computer-executable instructions to be executed by the processor 22. The memory 24 may include random access memory (RAM), flash memory, non-volatile random access memory (NOVRAM), and/or any other suitable form of memory.

Sensor data may include data gathered by sensors of the medical device 12 during a medical procedure. The sensor data may include an ambient temperature or humidity of the environment in which the medical device is operating, data regarding metrics of a patient's anatomy such as a temperature, hardness, density, conductivity, or resistivity of the patient's anatomy, a presence of one or more antibodies or hormones, a heart rate, or any other type of data regarding patient anatomy that may be gathered by sensors of the medical device 12 during a medical procedure. Patient data may include data for identifying patients and associating hospital patient database information therewith, such as name, date of birth, allergens, insurance coverage, medical history, or any other type of patient information. Patient data may be gathered by, for example, sensors, patient identification sources such as bar codes and RF tags, or input by medical personnel. Image data may include, for example, video or still images gathered by an endoscope, an ultrasound device, a magnetic resonance imaging machine, an x-ray device, a computer tomography device, or any other type of medical device 12 suitable for generating image data. Device usage data may include, for example, data gathered by sensors of the medical device 12 for measuring operation of the medical device 12 such as a rotation speed of an end effector, number of actuations, a time of usage of the medical device 12, a charge level of a battery, a number of procedures in which the medical device 12 has been used, or any other type of data related to the operation of the medical device 12.

In some embodiments, the medical device 12 may receive data from the edge communication device 14 through one or more data connections 18. The medical device 12 may receive data such as configuration data, software updates, or firmware updates, for example. The configuration data may change the operation of the medical device 12, the operation of the sensors of the medical device 12, or how data is gathered or formatted. In some embodiments, different cabling protocols may be utilized to exchange communication between the edge communication device 14 and the medical device 12.

The edge communication device 14 includes one or more device adaptors 20. The device adaptors 20 enable the edge communication device 14 to communicate with devices other than the medical device 12 (e.g., data consuming devices 16). The device adaptors 20 are configured to receive data from the medical device 12 and transmit the data to other devices as described more fully herein. The device adaptors 20 may be wired or wireless adaptors that establish data connections with other devices using any suitable wired or wireless protocol. For example, the device adaptors 20 may establish data connections using Wi-Fi, Bluetooth, wired Ethernet (IEEE 802.3), powerline networking, Firewire, Universal Serial Bus (USB), serial, parallel, and/or any other suitable industry standard or proprietary protocol. In one embodiment, each device adaptor 20 includes one or more hardware components, such as one or more antennas, wired connection ports or terminals, or the like. One or more of the device adaptors 20 may also be configured to receive data, such as from a second edge communication device 14, from a networking device such as a router, from a second medical device 12, or from a hospital computer terminal or server. Although FIG. 1 illustrates the edge communication device 14 having three device adaptors 20, it should be recognized that the edge communication device 14 may have any number of device adaptors 20.

In some embodiments, the edge communication device 14 includes a processor 22 and a memory 24, such as processor 22b and memory 24b. The processor 22b is configured to execute computer-executable instructions perform the functions of the edge communication device 14. The computer-executable instructions may be stored within the memory 24b. Moreover, the processor 22b may be implemented on a chip such as a PCB, IC, or the like. In some embodiments, the processor 22b may be implemented on the same chip as the processor 22a. In other embodiments, the processor 22b and the processor 22a may be implemented on separate chips than one another. Further details of the edge communication device 14 are described below with reference to FIGS. 2-6.

The data consuming device 16 may be a second medical device 12, a hospital terminal or server, e.g. a health information technology (HIT) server, a cloud storage system, a healthcare system, a healthcare service, or any other suitable hardware and/or software component for consuming data received from the medical device 12. Herein, consuming data is defined as receiving and storing the data in the memory 24, formatting the data, processing the data, and/or otherwise manipulating data in any other way. Examples of consuming data include receiving, storing, and analyzing sensor data to assist in analyzing effectiveness of a medical procedure performed by the medical device 12 or to assist in diagnosing medical issues of a patient. Other examples of consuming data further include receiving new patient information gathered by the medical device 12 and storing or updating a patient information database, such as a patient information database stored within a hospital server or a cloud storage database. Consuming data may further include, for example, analyzing device usage data received from the medical device 12 to determine whether the medical device 12 needs maintenance or replacement, including performing predictive maintenance analytics. The hardware and software described in WO2018013666 for managing equipment are hereby incorporated herein by reference. Consuming data may also include receiving, storing, and/or formatting image data to assist in diagnosing a medical issue of a patient or presenting the image data to a physician or surgeon for assisting in diagnosing a patient issue or to prepare for further medical procedures. In one embodiment, the data consuming device 16 may be at a location which is geographically remote from the medical device 12. For example, the medical device 12 and the data consuming device 16 may be in different rooms or floors of a hospital or may be in different facilities, customer domains, or at a remote facility such as a cloud storage database.

Figure 2:
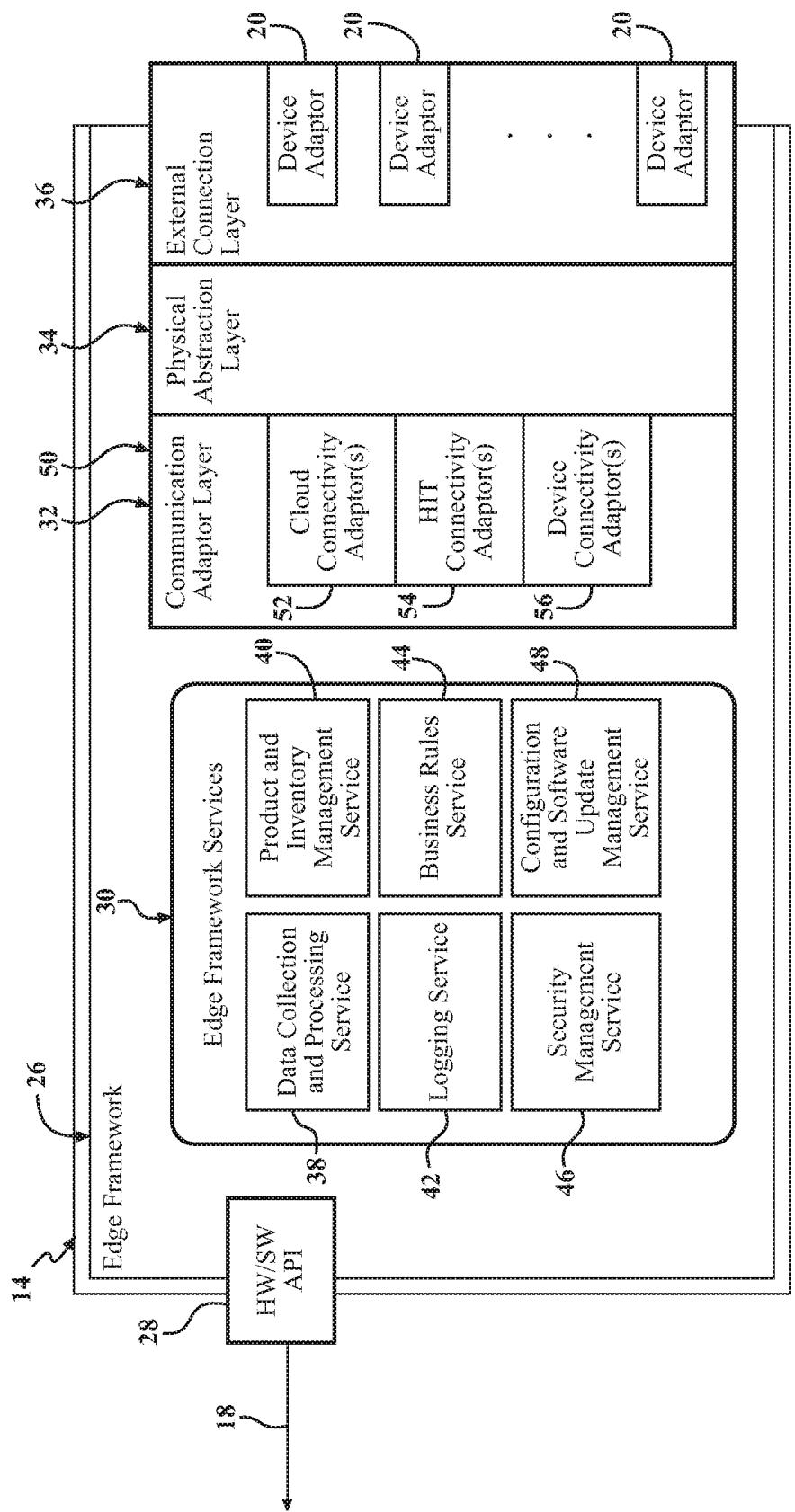
FIG. 2 is a block diagram of an edge framework that may be used with the system of claim 1.

FIG. 2 is a block diagram of the edge communication device 14 according to one embodiment. The edge communication device 14 is configured to receive data from the medical device 12 and transmit data received from the medical device 12 to a data consuming device 16. The edge communication device 14 is configured to receive, format, and transmit data from the medical device 12 according to a profile P.

In one embodiment, the profile P includes configuration data within a file (or multiple files) stored in a memory 24b of the edge communication device 14. The configuration data of the profile P may include one or more of the data available from the medical device 12 (e.g., the types of data available), a format of the data provided from the medical device 12 and/or a format of the data that the medical device 12 can accept, a set of services available on the medical device 12, and a set of services available remotely about the medical device 12. The configuration data of the profile P may also include or identify a network location of the edge communication device 14 and/or the medical device 12 coupled to the edge communication device 14, a communication path between the edge communication device 14 and one or more data consuming devices 16, a version of one or more services, software modules, or other components of the edge communication device 14 or medical device 12, a list of authorization levels for one or more types of data provided by the medical device 12 and/or stored in the edge communication device 14, and/or any other suitable data. The profile P may be configurable and/or updateable during runtime of the edge communication device 14 (i.e., after the software of the edge communication device 14 has been compiled and installed on the edge communication device 14). For example, an external device or system may modify, delete, or add new configuration data of the profile P to add, modify, or remove functionality of the edge communication device 14 and/or the medical device 12 to which the edge communication device 14 is attached, as described more fully herein.

The profile P may differ according to the device on which the profile P is stored or the medical device 12 to which the edge communication device 14 is coupled, the medical company or hospital that owns and/or uses the medical device 12, the geographic region in which the medical device 12 is used, or a combination thereof. For example, the profile P used by edge communication devices 14 in a network in a first country or region may be different than the profile P used by edge communication devices 14 in a network in a second country or region. Accordingly, the profiles may differ by country or region to conform to laws and customs of each respective country, or to ensure that data generated in the first country or region, for example, is only transmitted to devices located in the first country or region, and that data generated in the second country or region is only transmitted to devices located in the second country or region. Similarly, a first medical company may use a different profile P for edge communication devices 14 operating within that company than a second medical company, the profiles P differing according to company policies and business practices.

In one embodiment, a default profile P may be initially distributed to edge communication devices 14. The default profile may contain default configurations for the edge communication device 14, such as default rules and connectivity configurations. The default configurations may be used until the default profile is modified or reconfigured. The default profile may or may not be specific to the type of device on which the default profile is stored. For example, some networks may load the default profile onto any new edge communication device 14 entering the network, regardless of whether the edge communication device 14 is coupled to a medical device. Conversely, some networks may load a default profile specifically configured for medical devices 12 onto new edge communication devices 14 coupled to medical devices 12 entering the network and may load a different default profile specifically configured for servers onto new edge communication devices 14 coupled to servers entering the network.

The edge communication device 14 includes an edge framework 26. The edge framework 26 includes a hardware/software application programming interface (API) 28, one or more edge framework services 30, a communication adaptor layer 32, a physical abstraction layer 34, and an external connection layer 36. The external connection layer 36 includes one or more device adaptors 20.

The hardware/software API 28 may be configured to interface with the medical device 12 for bidirectional data communication via the data connection 18. In some embodiments, the hardware/software API 28 includes hardware specifically configured for interfacing with the medical device 12 with which the edge communication device 14 is in communication. In some cases, the hardware/software API 28 is configured to include software that is standardized such that the software may be used to communicate with any type of medical device 12. For example, the hardware/software API 28 may include a set of standardized functions or drivers to enable the edge communication device 14 to receive data from any of a surgical tool, a computer terminal, a hospital bed, or a plurality of other medical devices 12 without needing to be specifically configured or programmed to communicate with the medical device 12. According to some aspects, the hardware/software API 28 may be configured such that the edge communication device 14 may communicate with one more devices (e.g., medical device, data consuming device, etc.) via a plurality of different protocols.

In some embodiments, the hardware/software API 28 may be updated via the profile P to enable the hardware/software API 28 to communicate with certain types of medical devices 12. For example, the profile P may be updated to enable the edge communication device 14 to receive and comprehend data from a hospital bed. More specifically, the profile P may be updated to identify the data format and communication protocol used by the hospital bed when transmitting data from the bed and may set a flag or configuration parameter to enable communication through the identified communication protocol. Updating the hardware/software API 28 may be necessary to receive and comprehend data from the hospital bed due to the format or communication protocol of the data gathered and transmitted by the hospital bed. For example, the hardware/software API 28 may need updated communication drivers (e.g., Bluetooth, Wi-Fi, wired Ethernet, etc.) to be provided in order to communicate with the hospital bed in the event that the hospital bed communicates via a different protocol than the edge communication device 14 is configured to receive.

The edge framework services 30 may include a data collection and processing service 38, a product and inventory management service 40, a logging service 42, a business rules service 44, a security management service 46, and a configuration and software update management service 48. The edge framework services 30 may be stored within the memory 24b of the edge communication device 14. Alternatively, in some embodiments, the edge framework services 30 may be stored within a memory shared between the edge communication device 14 and the medical device 12 (e.g., memory 24). Still alternatively, the edge framework services 30 may be distributed across multiple devices within the network hierarchy 62. Each of the edge framework services 30 may be implemented as computer-executable instructions, modules, or programs that are stored in the memory 24 of the edge communication device 14 and/or the medical device 12 and that are executable by the processor 22 of the edge communication device 14 and/or the medical device 12 to perform the functions described herein.

The edge framework services 30 may each be at least partially updated or reconfigured via the profile P, for example, and/or through one or more software updates received from an external device or system. In some embodiments, the edge framework services 30 include all of the data collection and processing service 38, the product and inventory management service 40, the logging service 42, the business rules service 44, the security management service 46, and the configuration and software update management service 48. In other embodiments, the edge framework services 30 include only one or more of the data collection and processing service 38, the product and inventory management service 40, the logging service 42, the business rules service 44, the security management service 46, and the configuration and software update management service 48.

The data collection and processing service 38 is configured to facilitate collecting and processing data received from the medical device 12. For example, the data collection and processing service 38 may identify a data format or protocol of the data received from the medical device 12, reformat the data into a common data format or a data format expected by a data consuming device 16, and store the reformatted data in the memory 24b internal to the edge communication device 14. The data collection and processing service 38 may also configure the edge communication device 14 to receive data from the medical device 12 at specified time intervals, or may implement any other suitable method of facilitating collecting and processing data received from the medical device 12. In some embodiments, the medical device 12 "pushes" data (i.e., initiates the transfer of the data) to the data collection and processing service 38 through the hardware/software API 28. In other words, the hardware/software API 28 receives the data and provides the data to the data collection and processing service 38 whenever the medical device 12 initiates the transfer of the data to the edge communication device 14. In other embodiments, the data collection and processing service 38 "pulls" data (i.e., initiates the reading or gathering of the data) from the medical device 12 by the hardware/software API 28. In other words, the data collection and processing service 38 requests data from the medical device 12 through the hardware/software API 28, and the medical device 12 transmits the data to the data collection and processing service 38 through the hardware/software API 28 after receiving a request from the data collection and processing service 38.

In some embodiments, the product and inventory management service 40 is configured to format data to facilitate inventory management within a hospital network, for example. The product and inventory management service 40 may format, or process device usage data to facilitate the hospital network managing inventory of the medical device 12 and similar medical devices 12 according to the device usage data. For example, the device usage data may indicate that the device requires maintenance or replacement, and the edge communication device 14 may format and process the device usage data to communicate with a central hospital server, enabling the central hospital server to update hospital-wide product and inventory management according to the need for maintenance or replacement of the medical device 12.

In other embodiments, the product and inventory management service 40 is configured to identify the medical device 12 and the edge communication device 14 to facilitate hospital inventory management. For example, the product and inventory management service 40 may transmit data identifying the medical device 12 and the edge communication device 14 to a hospital server, thereby enabling the hospital server to confirm that the medical device 12 and the edge communication device 14 are active, functioning, and located within the hospital. The hospital server may receive similar transmissions from other medical devices 12 and edge communication devices 14 to maintain a hospital-wide inventory database.

The logging service 42 formats the data received from the medical device 12 to create log files of the device before transmitting the log files to the data consuming device 16. In one embodiment, the logging service 42 receives a data stream from the medical device 12, formats the data included within the data stream, and stores the formatted data in one or more log files within the memory 24b of the edge communication device 14. Alternatively, the medical device 12 itself may generate one or more log files and may transmit the log files to the logging service 42 for storing and/or reformatting the log files by the logging service 42. For example, the data consuming device 16 may be a server within a cloud computing environment and the medical device 12 may be a surgical tool. The logging service 42 may create a log file of sensor data gathered by the surgical tool over a period of time during a surgical procedure and may store the log file in the memory 24b of the edge communication device 14. The logging service 42 may then transmit the log file to the server for storage and analysis. In some embodiments, the logging service 42 creates log files with data received from the medical device 12 and formats the data logs into a format suitable to the data consuming device 16. For example, the logging service 42 may execute one or more scripts, functions, or services on the data received from the medical device 12 to create one or more log files and to format the log files into a format suitable to the data consuming device 16 according to the profile P. In other embodiments, the logging service 42 may store the log files in a standard format that is common across medical devices 12, edge communication devices 14, and/or data consuming devices 16.

In one embodiment, the profile P may be updated to add new logging features to an edge communication device 14 (and, by extension, to its associated medical device 12). For example, an edge communication device 14 may not initially be configured to log data of a particular data type received from the medical device 12. A profile distribution system (described below) or another suitable service or device may transmit an update to the profile P to indicate that the data of the particular data type should be logged. In response, the logging service 42 may create one or more logs based on the associated data received from the medical device 12.

The business rules service 44 may be configured to implement one or more business rules stored in the profile P. For example, the profile P may identify a rule that all data corresponding to a particular data type or category of medical devices 12 should be transmitted to a particular data consuming device 16, such as a database server. The business rules service 44 may implement the rule by gathering the identified data and transmitting it to the identified data consuming device 16. The profile P may be updated to add, modify, or delete any such rules as desired.

In other embodiments, the business rules service 44 may apply an algorithm to data received from a medical device 12 to create new data. For example, the business rules service 44 may receive raw sensor data generated by the medical device 12 and apply an algorithm to create a rolling average of the data that is then stored within memory of the edge communication device 14 and that may be transmitted to one or more data consuming devices 16. In some embodiments, the business rules service 44 may be configured to apply a mathematical formula or algorithm to values from data received from the medical device 12, thereby creating a new type, format, or content of data that may be transmitted to the data consuming device 16. The business rules service 44 may perform data conversion, such as converting temperature data from degrees Celsius to degrees Fahrenheit. The business rules service 44 may also add a new post-release capability or intelligence feature to edge communication device 14, and by extension to the medical device 12, without needing to alter the medical device itself.

In some embodiments, the business rules service 44 may reduce a volume of data received from the medical device 12 before transmitting the data to a data consuming device 16, such as by applying a compression algorithm to the data. The business rules service 44 may also verify the validity of the data received from the medical device 12, or may apply boundary constraints to ensure that the data satisfies predetermined conditions. The business rules service 44 may perform computation on the data that would otherwise be performed elsewhere in the network, such as at one or more devices or servers within other portions of the network hierarchy 62. Performing this computation at the edge communication device 14 using the business rules service 44 may save time and money over performing the computation elsewhere in the network. In some embodiments, the business rules service 44 may monitor the data received from the medical device 12 to determine whether the data is indicative of a particular event occurring, such as a failure of a part of the medical device 12. If the business rules service 44 determines that the event has occurred or is occurring, the business rules service 44 may transmit a notification or command to the medical device 12, to the data consuming device 16, and/or to another device within the network hierarchy 62. In response, the device receiving the notification or command may monitor or verify data received from the medical device 12, or may disable or enable one or more features of the medical device 12, for example.

The security management service 46 may be configured to format the data according to one or more security protocols of the hospital and/or the network hierarchy 62 in which the medical device 12 is located or connected to before the data is transmitted to other devices within the network hierarchy 62. In some embodiments, the security management service 46 identifies a security protocol corresponding to the type of data received from the medical device 12 and may format the data according to the identified security protocol. Some data types, such as patient information, may require application of strict security protocols, while other types of data, such as device usage data, require no application of a security protocol. For example, the security management service 46 may identify a strict security protocol that requires patient information to be encrypted before the patient information is transmitted to the data consuming device 16. The security management service 46 may then encrypt any patient information before the patient information is transmitted to the data consuming device 16, thereby ensuring that the hospital security protocol is met.

In one embodiment, the security management service 46 implements an authentication and/or an authorization policy of the edge communication device 14. For example, the authentication policy may include a requirement that any data consuming device 16 that attempts to access data stored in, or provided by, the edge communication device 14 must be authenticated and must also be authorized based on an access level of the data consuming device 16. The authentication of data consuming devices 16 may be accomplished using digital certificates issued by a trusted authority, may be accomplished using public key infrastructure (PKI) keys, or by any other suitable method. The security management service 46 may determine an access level for the data consuming device 16 after the data consuming device 16 has been authenticated, for example. The access level of the data consuming device 16 may be stored in the profile P of the edge communication device 14, or may be stored in another portion of the edge communication device memory 24b. The access level needed to access data from the edge communication device 14 (or by extension, from the medical device 12 attached to the edge communication device 14) may be different based on the type of data provided by the edge communication device 14 or medical device 12. For example, patient information may require a relatively high level of access, while sensor data of the medical device 12 may require a relatively low level of access. If the security management service 46 determines that the data consuming device 16 has a sufficiently high access level corresponding to a type of data requested by the data consuming device 16, the security management service 46 may authorize the transmission of the requested data to the data consuming device 16. Conversely, if the data consuming device 16 has an insufficient access level in relation to the requested data, the security management service 46 may prevent the data consuming device 16 from receiving the requested data. It should be recognized that different data consuming devices 16 may have different access levels stored within a profile P of different edge communication devices 14.

Data consuming devices 16 may also be able to modify data or profiles P within an edge communication device 14 if the access level of the data consuming device 16 enables the modification. For example, in some embodiments, certain data consuming devices 16 may be able to modify a profile P of an edge communication device 14 to change a format used for transmitting data to that data consuming device 16, to add, modify, or delete certain types of data to be received by that data consuming device 16, or to change security keys or digital certificates stored and/or used by the edge communication device 14.

The authorization and authentication functions of the security management service 46 may be configured and updated through the profile P. For example, the profile P may be updated to change a list of authorized devices for accessing data of the edge communication device 14, or may be updated to change an access level for one or more devices. In addition, the profile P may be updated to modify a type of encryption used by the security management service 46, such as by increasing the encryption from 128 bit to 256 bit encryption. The profile P may also be modified to add or change a digital certificate, security key, or other security mechanism applied to data received by and/or transmitted to the edge communication device 14 on which the profile P is stored.

The security management service 46 may also enable the edge communication device 14 to add new functionality based on updates to the profile P. For example, in one embodiment, the edge communication device 14 may not initially implement encryption for certain data transmitted to the data consuming devices 16. A profile distribution system (discussed below) may implement a network-wide security policy that requires all data of an identified data type (e.g., patient information) to be encrypted before being transmitted to any data consuming device 16. The profile distribution system may then update the profile P of the particular edge communication device 14 to indicate that the edge communication device 14 should encrypt all data corresponding to the identified data type according to an identified encryption algorithm. The profile distribution system may also transmit one or more cryptographic keys to the edge communication device 14 to enable the encryption. The security management service 46 may then encrypt the data transmitted from the edge communication device 14 according to the identified encryption protocol. It should be recognized that this added functionality (i.e., the encryption of data) may be implemented without modifying software executing on the medical device 12, e.g., without modifying software instructions executed to perform medical device operations regulated by a certain agency. Accordingly, the medical device 12 may not need to undergo re-certification in this example.

The configuration and software update management service 48 may be configured to manage software updates and related configuration details of the edge communication device 14 and/or the medical device 12 coupled to the edge communication device 14. For example, the configuration and software update management service 48 may interface with an external server or profile management system to receive updates to the edge framework services 30 or other software components of the edge framework 26. The configuration and software update management service 48 may also store data identifying the current versions of software installed on the edge communication device 14 and/or the medical device 12. The configuration and software update management service 48 may transmit data representative of the software versions to an external server to compare the versions to a baseline software configuration for the edge communication device 14 or medical device 12. In a specific embodiment, a regulatory agency may validate or approve a particular software and/or hardware configuration of one or more edge communication devices 14 or medical devices 12, and data identifying the validated configuration may be stored by the external server. In such as an embodiment, the particular software and/or hardware configuration of an edge communication devices 14 and/or a medical device 12 may be updated without impacting certain functions of the medical device 12, e.g., medical device functions regulated by an agency such as the FDA.

When the edge communication device 14 begins operating (e.g., after a shutdown or reboot), the configuration and software update management service 48 may transmit a configuration snapshot, i.e. data representative of the current version of the edge communication device 14 software and/or hardware to the external server. The external server may be configured to store one or more validated configuration baselines for each medical device 12 and/or edge communication device 14. The validated configuration baselines are stored configurations of the edge communication device 14 and/or the medical device 12 that identify features or components of the edge communication device 14 and/or medical device 12 that have previously been validated. For example, the validated configuration baselines may include a list of peripheral devices or software components that have been validated for use with the medical device 12 and/or edge communication device 14. The external server may then compare the configuration snapshot to one or more of the validated configuration baselines. If the configuration snapshot matches the one or more validated configuration baseline, the external server may validate the edge communication device 14 to enable the edge communication device 14 and/or the medical device 12 to continue operating. Conversely, if the configuration snapshot does not match one of the validated configuration baselines, the edge communication device 14 and/or the medical device 12 or features or functions thereof may be prevented from operating until the software or hardware configuration is updated to match one of the validated configuration baselines.

The communication adaptor layer 32 includes one or more connectivity adaptors 50. The connectivity adaptors 50 are software drivers or interfaces that format data to be transmitted through the device adaptors 20 according to the type and format of the data, the individual device adaptors 20 through which the data will be transmitted, and the protocol by which the data will be transmitted. The connectivity adaptors 50 may include one or more cloud connectivity adaptors 52, HIT connectivity adaptors 54, and/or device connectivity adaptors 56. In one embodiment, the communication adaptor layer 32 may select a connectivity adaptor 44 for transmitting data to a data consuming device 16 based on the type of data to be transmitted, based on the particular data consuming device 16 that will receive the data, and/or based on an identified communication path through the network hierarchy 62 between the edge communication device 14 and the data consuming device 16.

The communication adaptor layer 32 may select any number of suitable connectivity adaptors 44 for simultaneously transmitting data to the data consuming device 16. The connectivity adaptors 44 selected can be wired, wireless, or a combination thereof. The connectivity adaptors 44 selected may each transmit the same set of data (i.e., duplicate data) from the same medical device 12, or may transmit the same data from multiple medical devices 12 (i.e., such that the same data is routed through multiple edge communication devices 14 in transit to a particular data consuming device 16 or a particular group of data consuming devices 16). For example, the connectivity adaptors 44 may transmit duplicate data (i.e., the same data received from the medical device 12 coupled to the edge communication device 14 or from two or more medical devices 12 or edge communication devices 14) to the same data consuming device 16 in order to improve integrity of the data being transmitted. Alternatively or additionally, the connectivity adaptors 44 may transmit different data in order to improve efficiency of data transmission.

The cloud connectivity adaptor 52 includes a software driver or interface that formats the data received from the medical device 12 to be transmitted to the cloud storage system through one or more of the device adaptors 20 configured to communicate with the cloud storage system. In one embodiment, the cloud connectivity adaptor 52 selects a device adaptor 20 that uses an Ethernet protocol (e.g., TCP/IP, UDP, etc.) to communicate with the cloud storage system and formats the data to be transmitted to the cloud storage system to conform to the Ethernet protocol. The HIT connectivity adaptor 54 includes a software driver or interface that formats the data received from the medical device 12 to be transmitted to the hospital server, e.g. the HIT server, through one or more of the device adaptors 20 configured to communicate with the HIT server. In one embodiment, the HIT connectivity adaptor 54 selects a device adaptor 20 that uses an Ethernet protocol or a suitable proprietary hospital communication protocol to communicate with the HIT server and formats the data to be transmitted to the HIT server to conform to the Ethernet or hospital communication protocol. In a similar manner, the device connectivity adaptor 56 includes a software driver or interface that formats the data received from the medical device 12 to be transmitted to a second medical device (e.g., medical device 12 or data consuming device 16) through one or more of the device adaptors 20 configured to communicate with the second medical device. In one embodiment, the device connectivity adaptor 56 selects a device adaptor 20 that uses a protocol specific to the second medical device 12 (e.g., Firewire, USB, a proprietary serial communication protocol, etc.) to communicate with the second medical device and formats the data to be transmitted to the second medical device to conform to the appropriate protocol. While the connectivity adaptors 50 have been described as including one or more cloud connectivity adaptors 52, HIT connectivity adaptors 54, and/or device connectivity adaptors 56, it should be recognized that any suitable adaptor may be used in addition to, or in place of, the identified adaptors.

In one embodiment, the connectivity adaptors 50 are configured to format data received from the medical device 12 to be transmitted to the data consuming device 16 according to the profile P. For example, in one embodiment, the profile P may identify a protocol or data format usable by the data consuming device 16 that will receive the data. The one or more connectivity adaptors 50 may then format the data received from the medical device 12 before transmitting the data to the data consuming device 16 if the data is in a format that is incompatible with the format used by the data consuming device 16. The format may be incompatible with the format used by the data consuming device 16 if the data consuming device 16 cannot effectively receive, store, process, or otherwise handle the data received from the medical device 12 in the format originally provided by the medical device 12 or the edge communication device 14.

In one embodiment, the profile P may be modified to add, remove, or modify one or more connectivity adaptors 50 to modify communication pathways or protocols the edge communication device 14 is able to use to communicate with data consuming devices 16. Newly added connectivity adaptors 50 may use the same underlying hardware or device adaptor 20. For example, a wireless connectivity adaptor 50 may be added that uses the same antenna as a previously existing connectivity adapter 50 in an edge communication device 14, and two or more connectivity adaptors 50 using the same underlying hardware or device adaptor 20 may be operated in parallel (e.g., by implementing virtual adaptors or the like).

The edge communication device 14 includes both software and hardware for defining and facilitating functionality of the edge communication device 14. In some embodiments, the hardware and/or software of the edge communication device 14 is separated and isolated from the medical device 12. For example, certain components (e.g., processor 22b and/or memory 24b) of the edge communication device 14 may be implemented on a separate circuit board than certain components (e.g., processor 22a and/or memory 24a) of the medical device 12. In other embodiments, the edge framework 26 shares hardware with the medical device 12, such as the processor 22, the memory 24, and the device adaptors 20. In some embodiments, the edge framework 26 and the medical device 12 may share a housing. These various embodiments are described with reference to FIGS. 3-6.

Figure 3:
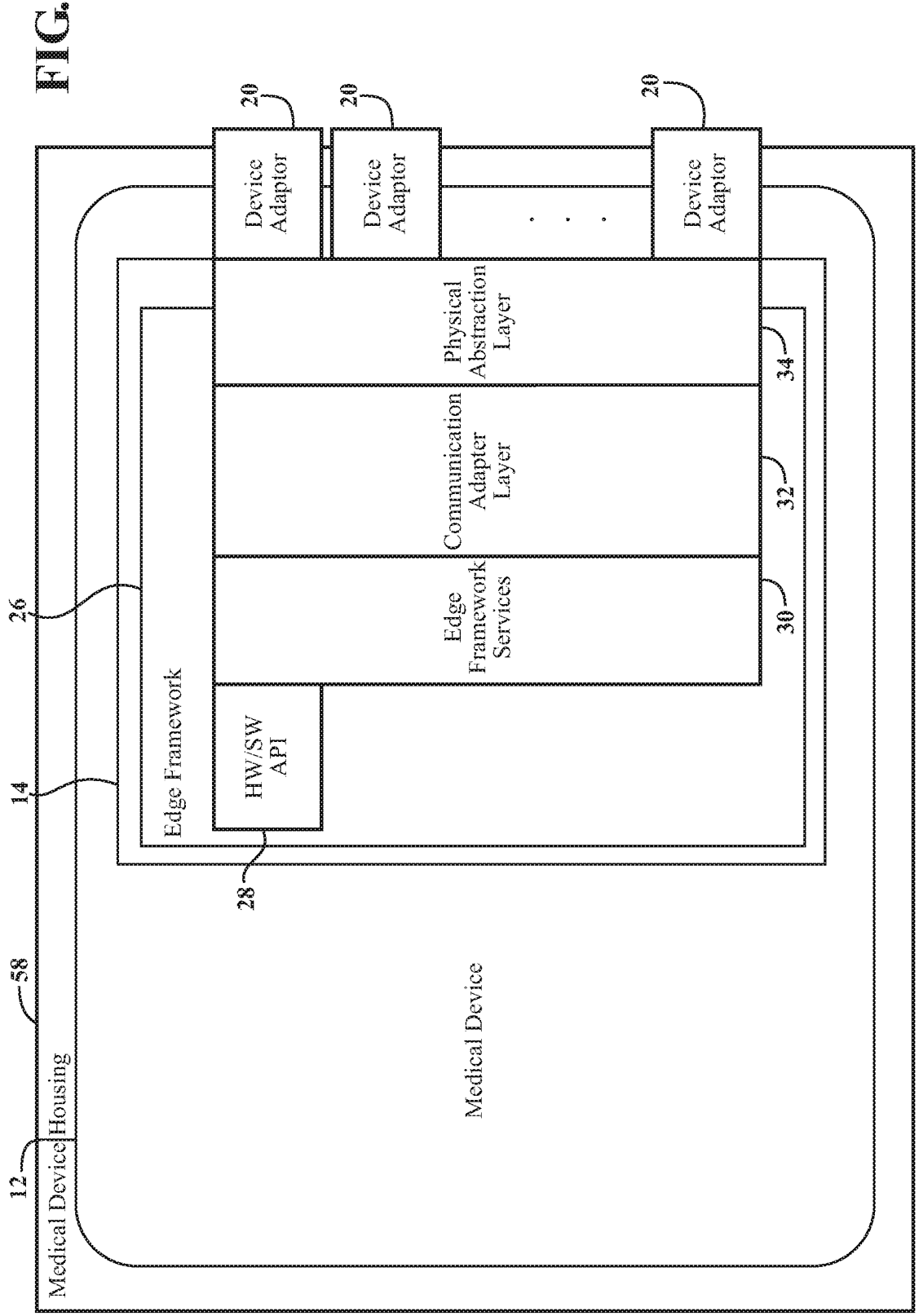
FIG. 3 is a block diagram of the medical device and the edge communication device integrated therein.

Referring to FIG. 3, in some embodiments the edge communication device 14 is fully incorporated within the medical device 12. The edge framework 26 is stored within the memory 24a of the medical device 12, and the edge framework services 30 are executed by the processor 22a of the medical device 12. The medical device 12 and the edge communication device 14 are both encased in a single housing of the medical device 12 (referred to as the medical device housing 58). Of course, the housing may have any suitable shape or configuration. The one or more device adaptors 20 are integral with or extend from the housing 58. Optionally still, the medical device may not necessarily include a housing, or the respective processors may not necessarily need to be disposed within housings, or at least within a common housing.

Figure 4:
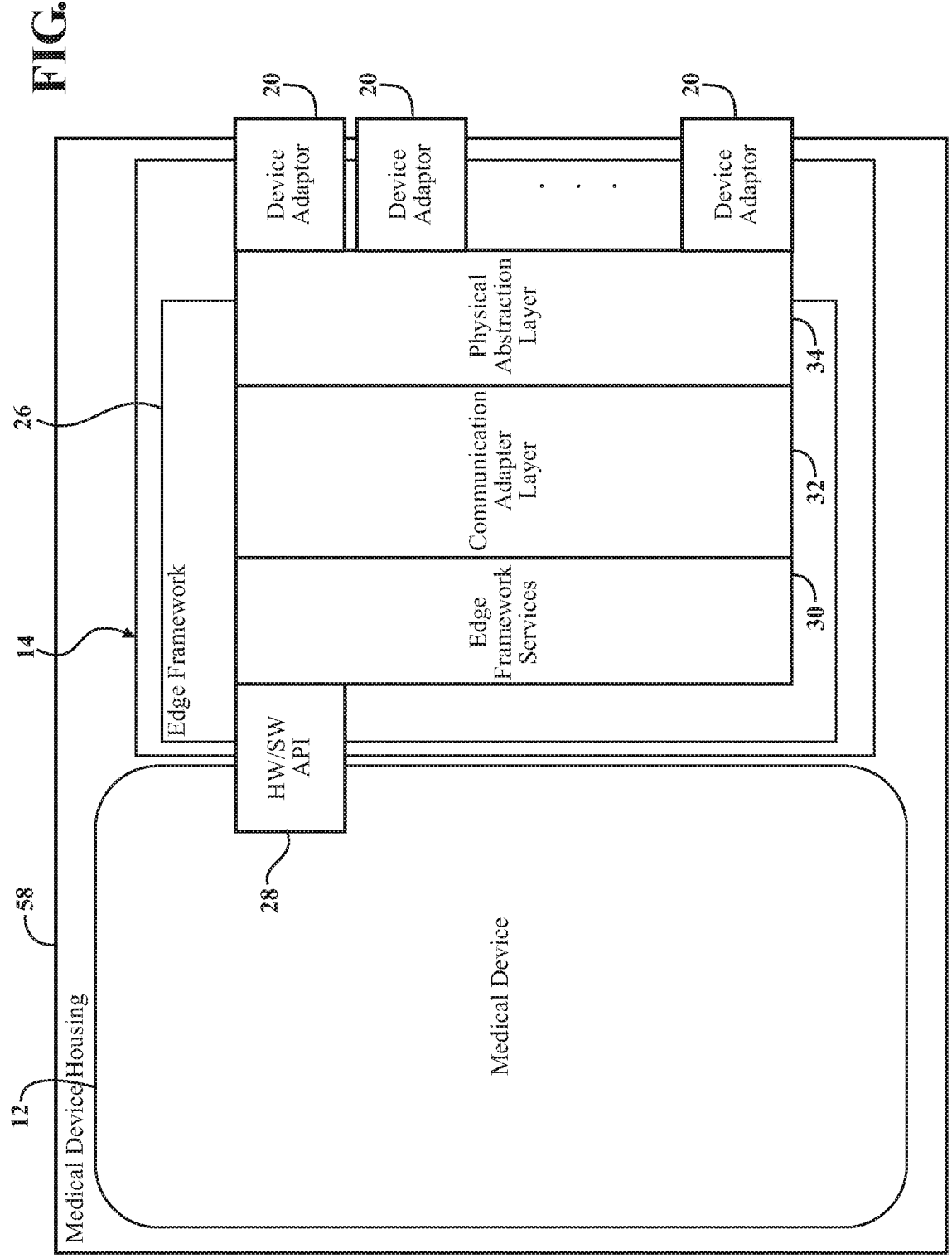
FIG. 4 is a block diagram of the medical device and the edge communication device positioned within a common housing.

Referring to FIG. 4, in some embodiments the edge communication device 14 is partially separated from the medical device 12. For example, the edge communication device 14 may be partially separated from the medical device 12 such that the medical device 12 and the edge communication device 14 each have a separate processor 22a, 22b and memory 24a, 24b, while the medical device 12 and the edge communication device 14 may both be encased in the medical device housing 58 or in another suitable housing. In one implementation, the medical device 12 and the edge communication device 14 may be encased in the same medical device housing 58, but the processor 22a and memory 24a of the medical device 12 may be implemented on a separate chip or circuit board than the processor 22b and memory 24b of the edge communication device 14. In some embodiments, the medical device housing 58 defines a cavity in which the edge communication device 14 may be removably inserted or fixedly attached, thereby connecting the edge communication device 14 to the medical device 12.

Figure 5:
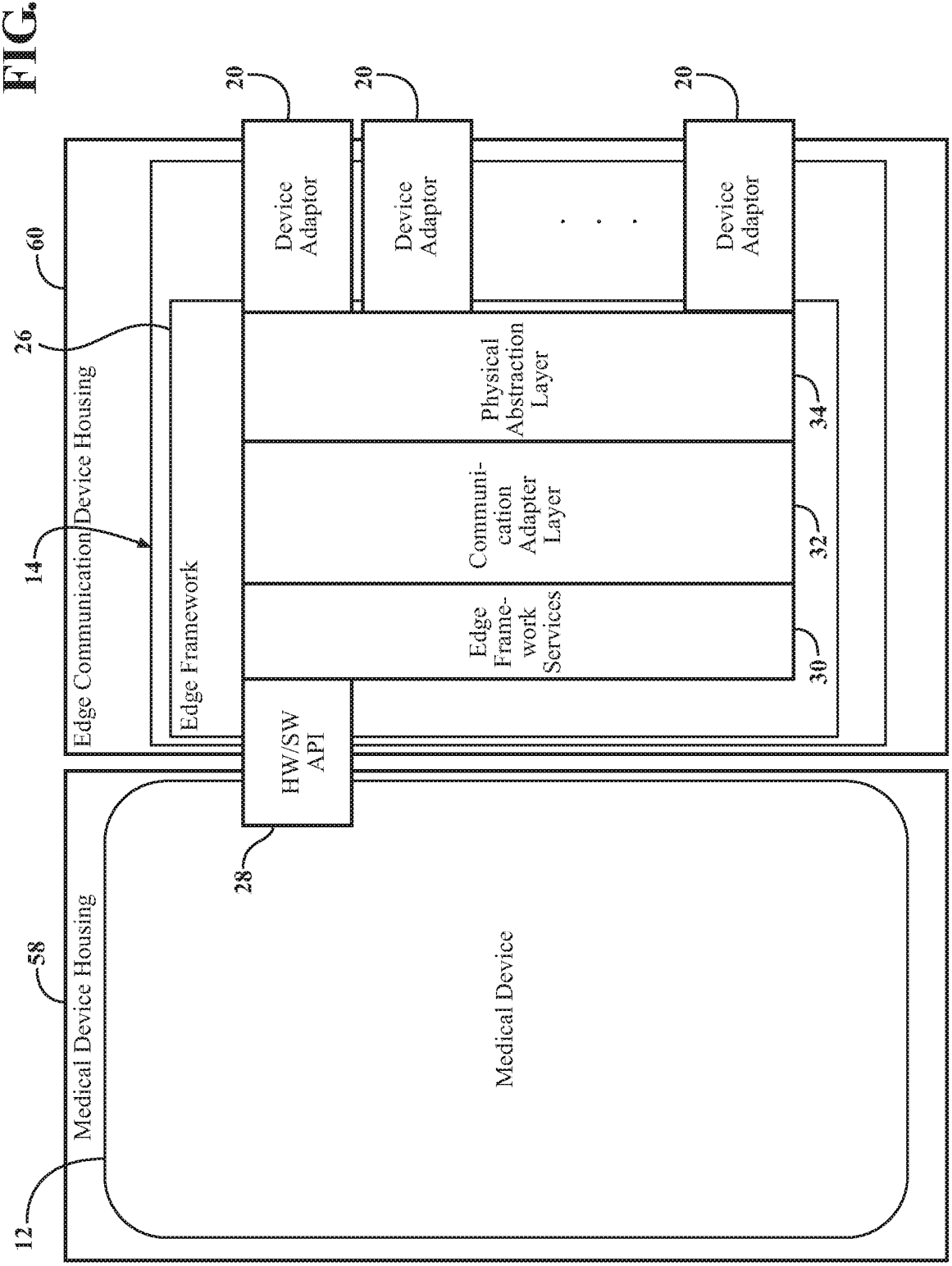
FIG. 5 is a block diagram of the medical device and the edge communication device positioned within separate housings that are coupled together.

Referring to FIG. 5, in some embodiments, the edge communication device 14 may be external to the medical device 12. For example, the medical device 12 may be included within the medical device housing 58 and the edge communication device 14 may be included within a separate edge communication device housing 60. The medical device housing 58 and the edge communication device housing 60 may be coupled together via the hardware/software API 28 and the data connection 18. In this embodiment, the medical device 12 includes a first processor 22a and a first memory 24a and the edge communication device 14 includes a second processor 22b and a second memory 24b. The edge communication device 14 may be removably connected to the medical device 12 using a suitable connector.

Figure 6:
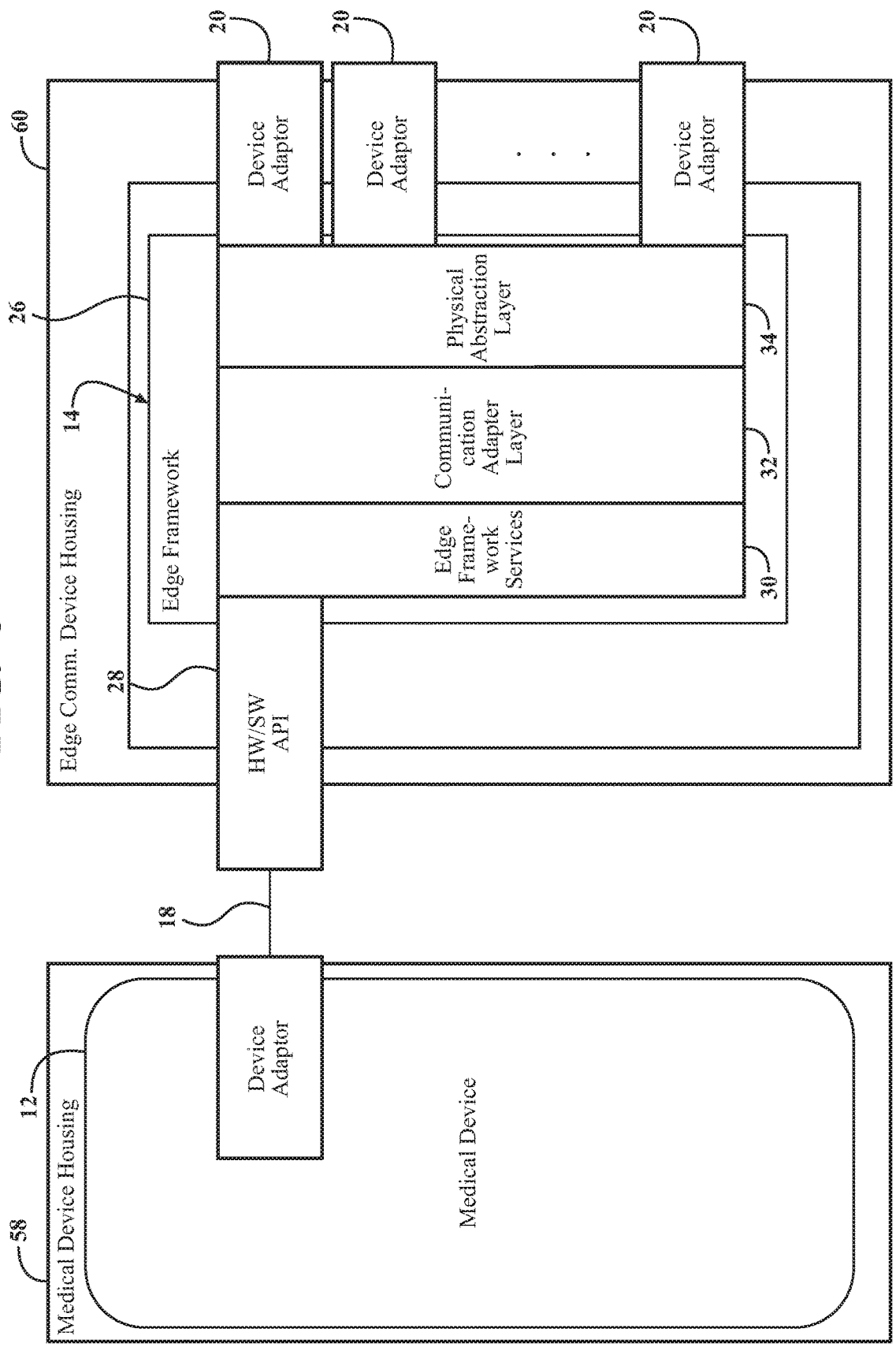
FIG. 6 is a block diagram of the medical device and the edge communication device positioned remotely from each other.

Referring to FIG. 6, in some embodiments, the edge communication device 14 is located remotely from the medical device 12. For example, the medical device 12 may be located remotely from the edge communication such that the edge communication is in a same room as the medical device 12, on a same floor as the medical device 12, within a same building as the medical device 12, on a same campus as the medical device 12, or distant from the hospital campus in which the medical device 12 is located. In this example, the medical device 12 may be connected to the network hierarchy 62 via the edge communication device 14 and may transmit data gathered by the medical device 12 to the edge communication device 14 via the data connection 18 in a wired or wireless manner. The medical device 12 may include a first processor 22a and a first memory 24a and the edge communication device 14 may include a second processor 22b and a second memory 24b. The medical device 12 may be positioned within the medical device housing 58 and the edge communication device 14 may be positioned within the edge communication device housing 60. In some embodiments, the edge communication device housing 60 may be and/or comprise an adapter, dongle, or any suitable component configured to establish the data connection 18 between the edge communication device 14 and the medical device 12.

Figure 7:
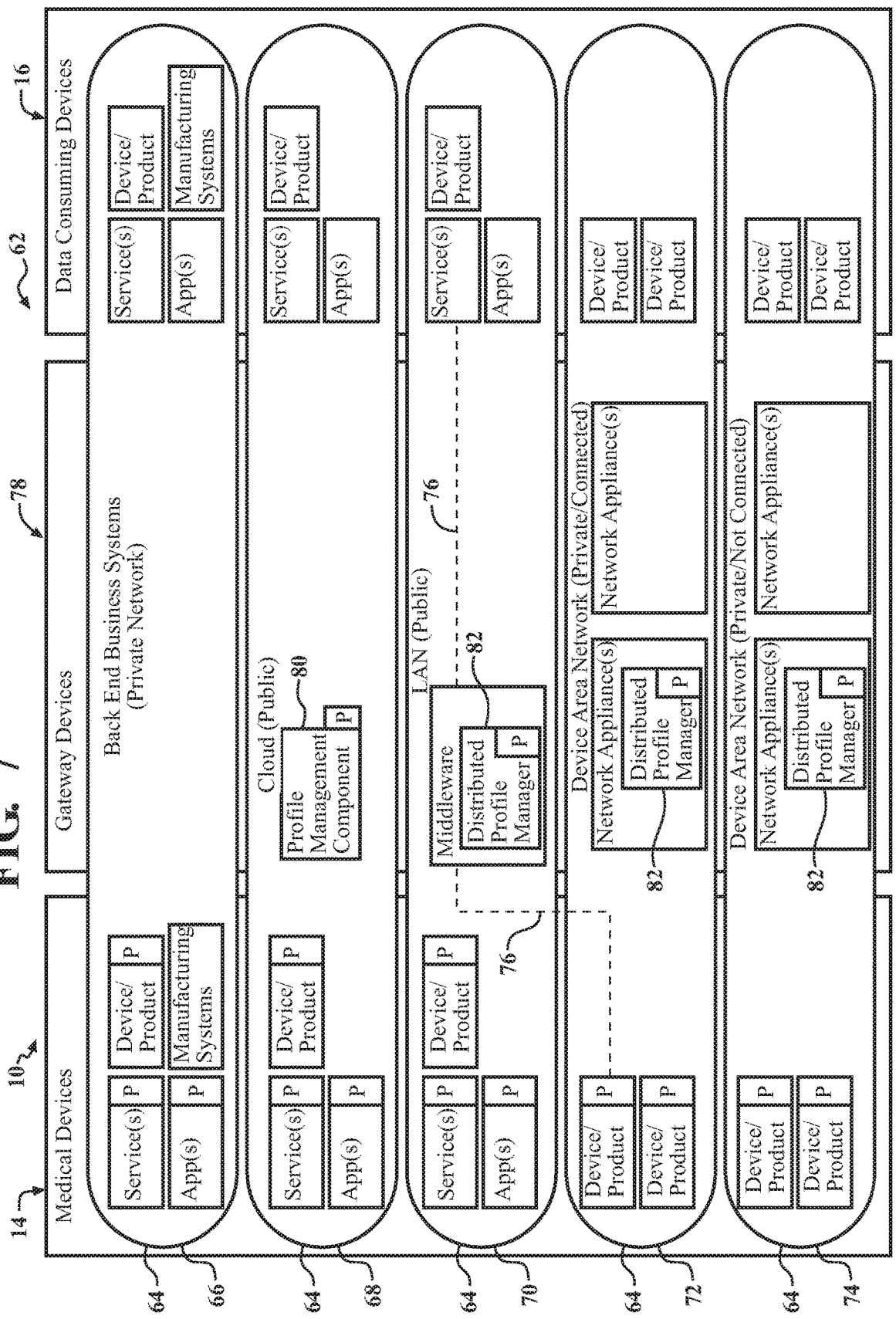
FIG. 7 is a block diagram of a network hierarchy including a plurality of medical devices and data consuming devices.
Figure 8:
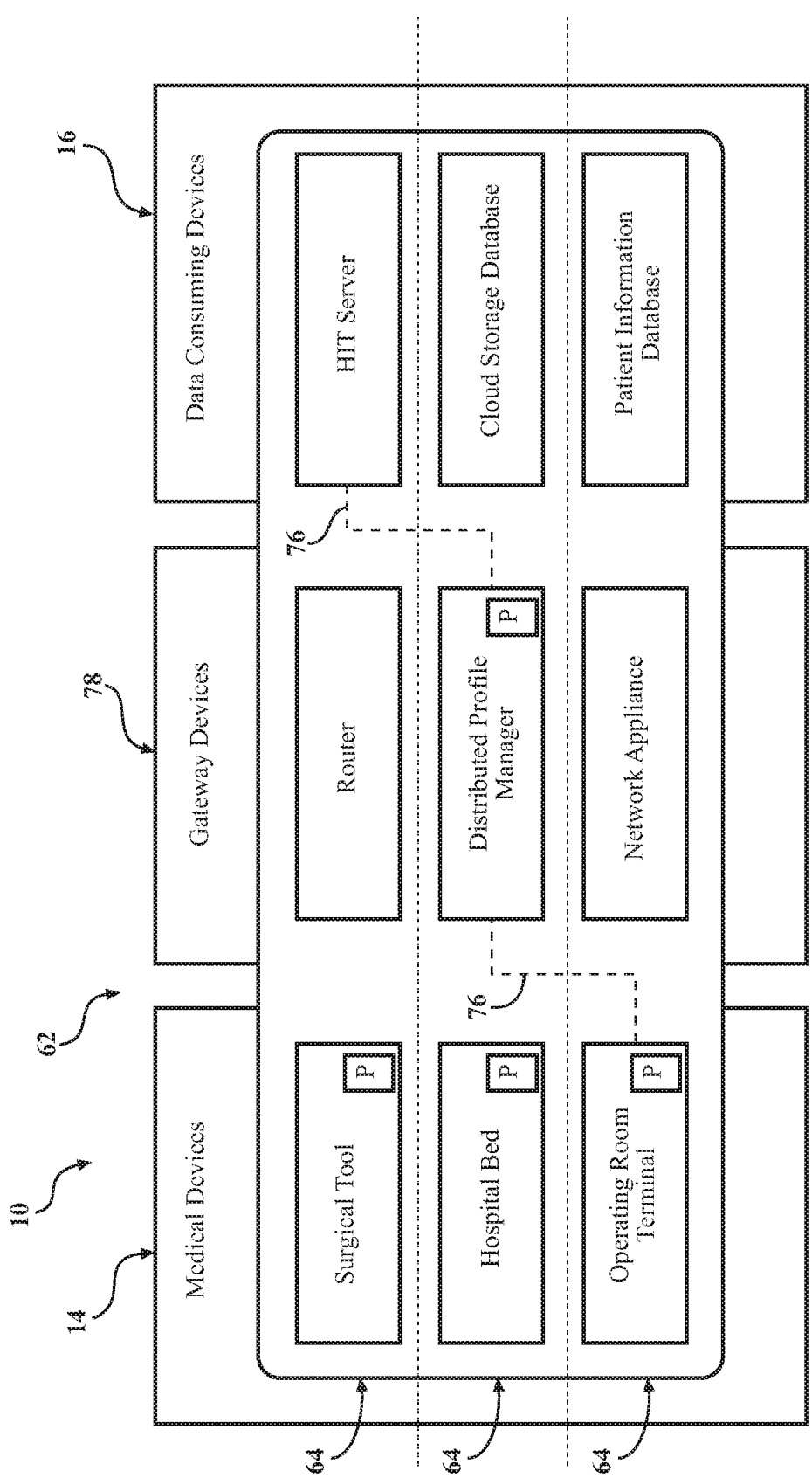
FIG. 8 is a block diagram of a portion of the network hierarchy.

FIGS. 7 and 8 illustrate portions of a network hierarchy 62 to which a plurality of edge communication devices 14 and a plurality of data consuming devices 16 are connected and over which the edge communication devices 14 and the data consuming devices 16 communicate. The network hierarchy 62 includes a plurality of network layers 64, and each network layer 64 may include one or more networks. The network layers 64 may include a back end business network 66, a cloud network 68, a local area network (LAN) 70, a connected device area network 72, an unconnected device area network 74, and/or any other suitable network.

The network hierarchy 62 includes a plurality of medical devices 12 connected to one or more data consuming devices 16 within one or more networks of the network hierarchy 62 via a plurality of edge communication devices 14 and one or more gateway devices 78. The data consuming devices 16 may receive data from one or more medical devices 12 via one or more of the gateway devices 78. The gateway devices 78 may include network appliances, devices running middleware, devices running profile management components, or any other suitable devices that enable devices within the network hierarchy 62 to communicate with each other across networks or network layers 64. For example, the gateway devices 78 may be embodied as one or more gateways, routers, switches, or other network appliances that enable data to be routed and/or translated across various networks, network layers 64, and/or devices within a communication path between an edge communication device 14 and a data consuming device 16. As a further example, the edge communication device 14 may transmit data to network appliance such as a router. The router may then transmit the data to the data consuming device 16, e.g. a hospital server, through at least a portion the communication path. In some embodiments, the gateway devices 78 may also act as data consuming devices 16. For example, a HIT server may be enabled to route data between the edge communication device 14 and the data consuming device 16, and may also be enabled to receive data from the edge communication device 14 and store the data, format the data, process the data, or otherwise manipulate the data.

The edge communication device 14 transmits data received from the medical device 12 to the data consuming device 16 through a communication path 76. In one embodiment, the communication path 76 is at least partially defined according to the profile P. The communication path 76 may include the edge communication device 14, the data consuming device 16, and any number of gateway devices 78 disposed between the edge communication device 14 and the data consuming device 16. The communication path 76 may include devices positioned at different network layers 64. The profile P may define the communication path 76 by identifying which, if any, gateway devices 78 will be used to transmit the data from the medical device 12 to the data consuming device 16. The profile P may also identify which data formats are understood and transmittable by the edge communication device 14, the gateway devices 78, and the data consuming device 16. For example, the medical device 12 may be a surgical tool. The surgical tool may gather sensor data during a surgical procedure and transmit the sensor data to the edge communication device 14 via the data connection 18. The profile P may specify that the sensor data is to be transmitted to a HIT server located within the local area network 70, for example. The profile P identifies the communication path 76 including gateway devices 78 between the edge communication device 14 and the HIT server on the network hierarchy 62, such as a router within an operating room and a communications server on a wing of the hospital on which the operating room is situated. The edge communication device 14 is configured to format the sensor data using one of the edge framework services 30, such as the data collection and processing service 38 or the logging service 42 and transmit the sensor data to the HIT server via the router and the communications server according to the communication path 76.

In some embodiments, the profiles P are managed and distributed by a profile distribution system 80 such that the profile distribution system 80 may operate as a centralized platform for adding, modifying, or removing functionality of edge communication devices 14 through updates to their respective profiles P. In one embodiment, the profile distribution system 80 includes one or more applications or programs executing on one or more servers in a cloud environment. Alternatively, the profile distribution system 80 may include one or more applications or programs executing on one or more other devices or computers within network hierarchy 62 in a distributed or centralized manner. The profile distribution system 80 may include a profile manager 82 that is distributed among one or more devices within the network hierarchy 62. For example, the profile manager 82 may be distributed among the gateway devices 78 to facilitate managing the profiles within the different network layers 64. The distributed profile managers 82 of the various gateway devices 78 are programs or services that may facilitate identifying communication paths 76 from devices at the same network layer 64 as the gateway device 78 and devices at a lower network layer 64 than the gateway device 78. The profile distribution system 80 may distribute profiles P and profile updates to the edge communication devices 14 based upon predictive algorithms that may optimize data flow based upon network hierarchy 62 needs. For example, the profile distribution system 80 may adjust communication paths 76 defined within one or more profiles P within one or more networks or network layers 64 to avoid network congestion that may arise within the network hierarchy 62.

The profile distribution system 80 may also manage the identification and updating of communication paths 76 between devices and may manage the updating of the profiles P of edge communication devices 14 to reflect the communication paths 76. For example, the profile distribution system 80 may initiate a network discovery process in which each network layer 64, each network, and each device within each network is identified and located within the network hierarchy 62. The profile distribution system 80 may then transmit updates to each profile P identifying the network location of each edge communication device 14 and/or medical device 12. The updates to the profiles P may also include updates to the communication paths 76 between data consuming devices 16 and edge communication devices 14 of medical device 12, or between any other suitable devices. The profiles P may be broken into pieces, and each piece may have a level of duplication with other profiles P. The profile distribution system 80 may distribute any number of profiles P, profile pieces, and profile updates as needed to maintain an efficient network hierarchy 62.

The profile distribution system 80 may also adjust the distribution of profiles P as necessary based upon new devices or services added to the network hierarchy 62. For example, if a new gateway device 78 is added to a network within the network hierarchy 62, the profile distribution system 80 may update the profiles P within the network hierarchy 62 to account for one or more additional communication paths that may arise due to the addition of the gateway device 78. In addition, if a new service or communication protocol is added to a medical device 12 or exposed by a medical device 12, the profile distribution system 80 may update the profile P of the edge communication device 14 coupled to that medical device 12 and/or the profiles P of other edge communication devices 14 to reflect the availability of the new service or communication protocol. In a similar manner, the profile distribution system 80 may update the profiles P within the network hierarchy 62 to reflect new network locations of one or more medical devices 12, edge communication devices 14, data consuming devices 16, and/or gateway devices 78 whenever a respective device is moved within a hospital or other portion of the network hierarchy 62, for example. In some implementations, the profile distribution system 80 may be configured to automatically implement adjustments and/or updates as described herein.

In one embodiment, the profile distribution system 80 may distribute profiles P and profile updates via the gateway devices 78. For example, the distributed profile manager 82 within each gateway device 78 may receive profile updates from the profile distribution system 80 and may forward the profile updates to the edge communication devices 14 connected to the respective gateway device 78. In some embodiments, the system 10 includes first and second edge communication devices 14 and first and second profiles P. The first and second profiles P may each define one or more communication paths 76 and data formats. The profile distribution system 80 may distribute the first and second profiles P to the first and second edge communication devices 14.

In some embodiments, the first profile P has a duplicable portion. The duplicable portion is a portion of the first profile P that may be transmitted from the first edge communication device 14 to the second edge communication device 14 and that may be incorporated into the second profile P. The duplicable portion may be incorporated into the second profile P by modifying the second profile P, e.g., overwriting a portion of the second profile P. For example, the first edge communication device 14 may be established within the network hierarchy 62 and the second edge communication device 14 may be newly added to the network hierarchy 62. While the second edge communication device 14 may be preloaded with a standardized or default profile P, the second edge communication device 14 may benefit from optimization included in a portion of the profile P used by the first edge communication device 14. The profile distribution system 80 may facilitate the first edge communication device 14 duplicating and transmitting the portion of the profile P of the first edge communication device 14 to the second edge communication device 14 for implementation therein.

In another embodiment, the profile P may include functionality that enables the data consuming device 16 to subscribe to data from a medical device 12 via an edge communication device 14 coupled to the medical device 12. The profile P of the edge communication device 14 may define one or more data collection parameters configured to manage the manner in which data is gathered and/or communicated via the system 10. For example, each edge communication device 14 may receive one or more data collection parameters specifying the type or content of the data, the amount or frequency of the data, and/or the data format to be transmitted to the data consuming device 16. In some implementations, a data collection parameter may specify one or more conditions (e.g., a threshold) associated with collecting data from the medical device 12 coupled to the edge communication device 14. For example, the data collection parameter may be such that the edge communication device 14 is only to transmit data to a data consuming device 16 when a condition or a set of conditions is met. Moreover, the edge communication device 14 may receive updates modifying one or more data collection parameters, e.g., according to the needs of at least data consuming device 16. By configuring the edge communication device 14 with a profile P, the system 10 may control the manner in which the edge communication device 14 gathers data from the medical device 12 and reports gathered data to the data consuming device 16, but without impacting the operation of the medical device 12 and/or changing software on the medical device 12.

In some embodiments, a profile P and an edge communication device 14 may be included within the gateway devices 78. The profile P and the edge communication device 14 may cause the gateway devices 78 to concatenate data that has been subscribed to when the data is being transmitted to the data consuming device 16. For example, the data consuming device 16 may subscribe to first and second data from the first and second edge communication devices 14, respectively. The first and second edge communication devices 14 may define first and second communication paths 76 and first and second data formats, respectively. The first and second data communication paths 76 may each include transmitting the data via the gateway device 78. The gateway device 78 may concatenate and manage the data before the data reaches the data consuming device 16.

In some embodiments, an edge communication device 14 having a first profile P may discover a new device, e.g. a new edge communication device 14, a new data consuming device 16, or a new gateway device 78. The new device may have a second profile P. The edge communication device 14 may communicate with the new device via the first and second profiles P. The edge communication device 14 may communicate with the new device to determine what data the new device has stored and may request the data the new device has stored.

The present disclosure has been described herein in an illustrative manner. It is to be understood that the terminology which has been used is intended to be in the nature of words of description rather than of limitation. Obviously, many modifications and variations of the disclosure are possible in light of the above teachings. The disclosure may be practiced otherwise than as specifically described within the scope of the appended claims.

One or more embodiments of the disclosure can be described with referenced to the following numbered clauses:

I. A system for communication of data, said system comprising:
 a medical device;
 a data consuming device positioned at a first network layer;
 an edge communication device positioned at a second network layer and in communication with said medical device to receive data from said medical device, said edge communication device having a profile defining a data format for the data and a communication path for transmitting the data between the network layers;
 a gateway device configured to route the data from said edge communication device to said data consuming device via said communication path,
 wherein said edge communication device is configured to modify the data format to correspond to the data consuming device and to format the data according to the data format.

II. The system of clause I, wherein the first and second network layers each include one of a back end network, a cloud-based network, a local area network, and a device area network.

III. The system of clause 1 and/or II, further comprising a profile distribution system positioned at one of said network layers.

IV. The system of any of clauses I-III, further comprising a second profile, wherein said gateway device is further configured to route said second profile to said edge communication device from said profile distribution system, said second profile defining a second communication path and a second data format.

V. The system of any of clauses I-IV, further comprising a second edge communication device positioned at the first network layer and in communication with said data consuming device to transmit data to said data consuming device.

VI. The system of any of clauses I-V, wherein said profile has a duplicable portion and said gateway device is further configured to route said duplicable portion to said second edge communication device, thereby at least partially creating a second profile defining a second communication path and a second data format.

VII. The system of any of clauses I-VI, wherein said gateway device includes a third edge communication device at a third network layer.

VIII. The system of any of clauses I-VII, wherein said third edge communication device has a second profile defining a second communication path and a second data format and said gateway device being further configured to route data from said third edge communication device to said data consuming device via said second communication path.

IX. The system of any of clauses I-VIII, wherein said edge communication device is in communication with said medical device via one of being integral with said medical device, being removably coupled to said medical device, and being wirelessly coupled to said medical device.

X. The system of any of clauses I-IX, wherein the data is collected from said medical device by said edge communication device.

XI. The system of any of clauses I-X, further comprising an API, wherein the data is pulled from said medical device by said edge communication device via said API.

XII. The system of any of clauses I-XI, wherein the data is pushed to said edge communication device by said medical device.

XIII The system of any of clauses I-XII, wherein the data includes at least one log file.

XIV. The system of any of clauses I-XIII, wherein said gateway device includes at least one intermediate device.

XV. The system of any of clauses I-XIV, wherein said gateway device is configured to route the data via said at least one intermediate device.

XVI. A system for communication of data, said system comprising:
 a medical device;
 at least one data consuming device;
 an edge communication device including a memory and a plurality of adaptors, said edge communication device being in communication with said medical device and each of said adaptors being configured to enable data communication with said at least one data consuming device via one or more of a plurality of protocols; and
 a profile stored in said memory, said profile being at least partially writable by a device remote from said edge communication device and said profile configuring said edge communication device to select one of said adaptors to enable data communication with said at least one data consuming device.

XVII. The system of any of clauses I-XVI, wherein said profile is configurable to enable data communication of a plurality of types.

XVIII. The system of any of clauses I-XVII, wherein said types include at least one of patient information and usage information of said medical device.

XIX. The system of any of clauses I-XVIII, wherein said profile configures said edge communication device to select one of said adaptors based upon one or more of said types of data communication.

XX. The system of any of clauses I-XIX, wherein said device remote from said edge communication device is said data consuming device.

XXI. The system of any of clauses I-XX, wherein said device remote from said edge communication device is different than said data consuming device.

XXII. The system of any of clauses I-XXI, wherein said profile is at least partially writable by said data consuming device in addition to said device remote from said edge communication device.

XXIII The system of any of clauses I-XXII, wherein said profile configures said edge communication device to select two or more adapters of said plurality of adaptors to enable data communication with said at least one data consuming device, each of said two or more adaptors being enabled to simultaneously communicate with said at least one data consuming device.

XXIV. The system of any of clauses I-XXIII, wherein said medical device is configured to transmit a set of data to said edge communication device, and wherein said two or more adaptors are enabled to simultaneously communicate the same set of data to said at least one data consuming device.

XXV. A system for data communication, the system comprising:
 a medical device comprising a primary processor configured to perform operational functions, a primary memory device programmed for performing operational functions, a first circuit board, one of the primary processor and primary memory device being mounted to the first circuit board;
 an edge communication device comprising:
 a secondary memory device,
 a transceiver configured to communicate with at least one data consuming device,
 a second circuit board, the secondary memory device and the transceiver mounted to the second circuit board, wherein the first circuit board is isolated from the second circuit board such that the secondary memory device is updateable without impacting regulated functions of the medical device, and
 a plurality of adapters configured to enable data communication between the transceiver and the at least one data consuming device,
 wherein the edge communication device is configured to select at least one adapter from the plurality of adapters to exchange data regarding the medical device with the at least one data consuming device; and
 a housing configured to encase the medical device and the edge communication device.

XXVI. The system of clause XXV, wherein the edge communication device further comprises an application programming interface (API) configured to enable bidirectional communication between the edge communication device and at least one of the medical device or the at least one data consuming device.

XXVII. The system of clause XXV and/or XXV, wherein the API includes software configured to enable communication between the edge communication device and a second data consuming device using a different communication protocol than that used between the edge communication device and the medical device.

XXIII The system of any of clauses XXV-XXVII, wherein the API enables the edge communication device to exchange data regarding the medical device via a plurality of different protocols.

XXIX. The system of any of clauses XXV-XXVIII, wherein the at least one data consuming device comprises one of a router, a gateway, a hospital computer terminal, a hospital server, a health information technology (HIT) server, or a cloud storage system.

XXX. The system of any of clauses XXV-XXIX, wherein the at least one data consuming device is at a location that is geographically remote from the medical device and the edge communication device.

XXXI. The system of any of clauses XXV-XXX, wherein the edge communication device is configured to select a first adapter and a second adapter from the plurality of adapters to communicate with the medical device and a second data consuming device, respectively, the first adapter being configured to enable communication between the edge communication device and the medical device using a first protocol, and the second adapter being configured to enable communication between the edge communication device and the second data consuming device using a second protocol different from the first protocol.

XXXII. The system of any of clauses XXV-XXXI, wherein the first protocol comprises a wired protocol, and wherein the second protocol comprises a wireless protocol.

XXXIII The system of any of clauses XXV-XXXII, wherein at least one of the first or second protocols comprise an Ethernet protocol, a Wi-Fi protocol, a Bluetooth protocol, a Universal Serial Bus (USB) protocol, or a FireWire protocol.

XXXIV. A system for data communication, the system comprising:
 a medical device;
 a data consuming device positioned at a first network layer;
 an edge communication device positioned at a second network layer and configured to communicate with the medical device, the edge communication device having a profile defining a communication path for transmitting data between the first and second network layers; and a gateway device configured to route data from the edge communication device to the data consuming device via the communication path.

XXXV. The system of clause XXXIV, wherein the first and second network layers each include one of a back end network, a cloud-based network, a local area network, or a device area network.

XXXVI. The system of clause XXXIV and/or XXXV, wherein the profile further defines a data format to be used to exchange information between the edge communication device and at least one of the medical device, the data consuming device, or the gateway device.

XXXVII. The system of any of clauses XXXIV-XXXVI, wherein the edge communication device is configured to receive configuration information modifying at least one data collection parameter associated with the medical device, the at least data collection parameter comprising one of a type of data or a frequency at which the type of data is to be communicated to the data consuming device.

XXXVIII. The system of any of clauses XXXIV-XXXVII, wherein the profile further defines a security policy requiring the edge communication device to encrypt one or more particular types of data to be transmitted to the data consuming device.

XXXIX. The system of any of clauses XXXIV-XXXVIII, wherein the edge communication device is configured to encrypt the one or more particular types of data according to an encryption algorithm specified by the security policy.

XL. The system of any of clauses XXXIV-XXXIX, wherein the edge communication device further comprises an application programming interface (API) configured to enable communication between the edge communication device and a second data consuming device using a different communication protocol than that used between the edge communication device and the medical device.

XLI. The system of any of clauses XXXIV-XL, wherein the at least one data consuming device comprises one of a router, a hospital computer terminal, a hospital server, a health information technology (HIT) server, or a cloud storage system.

XLII. The system of any of clauses XXXIV-XLI, wherein the edge communication device comprises a plurality of adapters configured to enable data communication via a plurality of protocols, respectively.

XLIII. The system of any of clauses XXXIV-XLII, wherein the edge communication device is configured to select a first adapter and a second adapter from the plurality of adapters to communicate with the medical device and a second data consuming device, respectively.

XLIV. The system of any of clauses XXXIV-XLIII, wherein the first adapter is configured to enable communication between the edge communication device and the medical device using a first protocol, and wherein the second adapter is configured to enable communication between the edge communication device and the second medical device using a second protocol different from the first protocol.

The invention claimed is:

1. A system for medical data communication in a surgical or medical environment, the system comprising:
    a medical device comprising a primary processor configured to perform first operational functions relating to regulated functions of the medical device, a primary memory device storing first computer-executable instructions that upon execution by the primary processor causes the primary processor to perform the first operational functions, and a first circuit board, the primary processor and the primary memory device being mounted to the first circuit board;
    an edge communication device coupled to the medical device and comprising:
        a secondary processor configured to perform second operational functions relating to communication of data regarding the medical device to a plurality of data consuming devices geographically remote from the edge communication device and the medical device;
        a secondary memory device, the secondary memory device storing computer-executable instructions that upon execution by the secondary processor causes the secondary processor to perform the second operational functions, and the second memory device also storing a profile defining a plurality of profile datums including:
            a consuming device datum identifying first and second data consuming devices subscribed to data from the medical device, the first data consuming device being subscribed to patient sensor data associated with the medical device to assist in treatment of the patient with the medical device, and the second data consuming device being subscribed to device usage data associated with the medical device to manage maintenance of the medical device,
            a communication path datum identifying first and second communication paths between the edge communication device and the first and second data consuming devices respectively,
            a communications protocol datum identifying first and second communications protocols for the first and second data consuming devices respectively, the first communications protocol differing from the second communications protocol,
            a security policy datum identifying first and second security policies for the patient sensor data and the device usage data respectively, the first security policy identifying an encryption algorithm to apply to the patient sensor data, and the second security policy indicating no encryption algorithm for the device usage data, and
            an access level datum identifying first and second access levels for the first and second data consuming devices respectively, the first access level allowing access to the patient sensor data stored on the edge communication device, and the second access level, different from the first access level, preventing access to the patient sensor data stored on the edge communication device;
        a transceiver configured to communicate with the first and second data consuming devices;
        a second circuit board, the secondary processor, the secondary memory device and the transceiver mounted to the second circuit board, wherein the first circuit board is isolated from the second circuit board such that each of the profile datums is updateable without impacting the regulated functions of the medical device; and
        first and second adapters configured to enable data communication between the transceiver and the first and second data consuming devices according to the first and second communications protocols for the first and second data consuming devices respectively, wherein the edge communication device is configured to communicate the patient sensor data and the device usage data associated with the medical device to the first and second data consuming devices respectively in accordance with the profile datums; and a housing configured to encase the medical device and the edge communication device, wherein responsive to the housing encasing the medical device and the edge communication device being moved from a first network to a second network, the edge communication device is configured to receive at least a portion of a second profile stored on a second edge communication device associated with another medical device on the second network, and adjust the profile datums stored in the edge communication device based on the at least a portion of the second profile.

2. The system of claim 1, wherein the edge communication device further comprises an application programming interface (API) configured to enable bidirectional communication between the edge communication device and at least one of the medical device or the data consuming devices.

3. The system of claim 2, wherein the API includes software configured to enable communication between the edge communication device and the medical device using a third communications protocol that differs from the first and second communications protocols.

4. The system of claim 1, wherein the edge communication device is configured to pull data from the medical device at a specified time interval, identify a format of the data from the medical device, and reformat the data into first and second data formats expected by the first and second data consuming devices respectively.

5. The system of claim 1, wherein the profile datums include a rule datum defining an algorithm to be applied to raw data from the medical device to generate, as at least a part of the patient sensor data, a rolling average of the raw data, and the edge communication device is configured to apply the algorithm to the raw data from the medical device.

6. The system of claim 1, wherein the first and second data consuming devices and the edge communication device are each disposed on a different network layer of a network hierarchy, the first defined communication path indicates a first gateway device for transmitting the patient sensor data from the edge communication device to the first data consuming device, and the second defined communication path indicates a second gateway device of the network hierarchy, different from the first gateway device, for transmitting the device usage data from the edge communication device to the second data consuming device.

7. The system of claim 6, wherein the first and second gateways each include a profile manager forming a profile distribution system of the network hierarchy, the edge communication device being configured to, responsive to being moved to a different one of the network layers of the network hierarchy, communicate with the profile distribution system to receive the at least a portion of the second profile.

8. The system of claim 6, further comprising the first and second gateways, wherein the first gateway is configured to receive the patient sensor data from the edge communication device, concatenate the patient sensor data with data received from a third edge communication device disposed in the network hierarchy, and communicate the concatenated data to the first data consuming device.

9. The system of claim 6, wherein the edge communication device is configured to communicate the patient sensor data to the first data consuming device via the first gateway in accordance with the profile, and communicate the patient sensor data to another edge communication device associated with another medical device for communication to the first data consuming device via an alternative communication path.

10. The system of claim 1, wherein the edge communication device is configured to adjust the profile datums based on the at least a portion of the second profile by modifying the encryption algorithm of the first security policy for the patient sensor data based on a corresponding encryption algorithm of the at least a portion of the second profile.

11. The system of claim 1, wherein the edge communication device is configured to adjust the profile datums based on the at least a portion of the second profile by replacing the first data consuming device identified in the profile with a third data consuming device identified in the second profile and replacing the second data consuming device identified in the profile with a fourth data consuming device identified in the at least a portion of the second profile.

12. A system for medical data communication in a surgical or medical environment, the system comprising:

a medical device; and an edge communication device attached to the medical device and located on a first network, the edge communication device configured to communicate with the medical device, and the edge communication device having a profile defining a plurality of profile datums including:

a consuming device datum identifying first and second data consuming devices subscribed to data from the medical device, the first data consuming device being located on a second network different from the first network and being subscribed to patient sensor data associated with the medical device for assisting in treatment of the patient with the medical device, and the second data consuming device being located on a third network different from the first and second networks and being subscribed to device usage data associated with the medical device to manage maintenance of the medical device, a communication path datum identifying first and second communication paths for transmitting the patient sensor data and the device usage data associated with the medical device to the first and second data consuming devices respectively, the first communication path identifying a first gateway device configured to route data between the first and second networks, and the second communication path identifying a second gateway device configured to route data between the first and third networks, a communications protocol datum identifying first and second communications protocols for the first and second data consuming devices respectively, the first communications protocol differing from the second communications protocol, a security policy datum identifying first and second security policies for the patient sensor data and device usage data respectively, the first security policy identifying an encryption algorithm to apply to the patient sensor data, and the second security policy indicating no encryption algorithm for the device usage data, and an access level datum identifying first and second access levels for the first and second data consuming devices respectively, the first access level allowing access to the patient sensor data, and the second access level, different from the first access level, preventing access to the patient sensor data, wherein responsive to the medical device being moved to a different network, the edge communication device is configured to communicate with a profile distribution system located on at least one of the first, second, or third networks to receive at least a portion of a second profile stored on a second edge communication device associated with another medical device on the different network, and adjust the profile datums stored in the edge communication device based on the at least a portion of the second profile.

13. The system of claim 12, wherein the profile further defines first and second data formats to be used to exchange information between the edge communication device and the first and second data consuming devices respectively.

14. The system of claim 12, wherein the access level datum further identifies a third access level different from at least one of the first access level or the second access level for a third data consuming device, the third access level allowing the third data consuming device to access the device usage data stored on the edge communication device and modify at least one data collection parameter associated with the medical device, the at least one data collection parameter comprising a type of data and a frequency at which the type of data is to be communicated to the first or second data consuming device.

15. The system of claim 12, wherein the edge communication device is configured to adjust the profile datums based on the at least a portion of the second profile by modifying the encryption algorithm of the first security policy for the patient sensor data based on a corresponding encryption algorithm of the at least a portion of the second profile.

16. The system of claim 12, wherein the edge communication device is configured to adjust the profile datums based on the at least a portion of the second profile by replacing the first data consuming device identified in the profile with a third data consuming device identified in the second profile and replacing the second data consuming device identified in the profile with a fourth data consuming device identified in the at least a portion of the second profile.

17. An edge communication device for medical data communication in a surgical or medical environment, the edge communication device being coupled to a medical device and comprising:

a processor configured to perform operational functions relating to communication of data regarding the medical device to a plurality of data consuming devices geographically remote from the edge communication device and the medical device;

a memory device storing computer-executable instructions that upon execution by the processor causes the processor to perform the operational functions, and the memory device also storing a profile defining a plurality of profile datums including:

a consuming device datum identifying first and second data consuming devices subscribed to data from the medical device, the first data consuming device subscribed to patient sensor data associated with the medical device for assisting in treatment of the patient with the medical device, and the second data consuming device subscribed to device usage data associated with the medical device to manage maintenance of the medical device based on the device usage data, a communication path datum identifying communication paths between the edge communication device and the first and second data consuming devices respectively, a communications protocol datum identifying first and second communications protocols for the first and second data consuming devices respectively, the first communications protocol differing from the second communications protocol, a security policy datum identifying first and second security policies for the patient sensor data and the device usage data respectively, the first security policy identifying an encryption algorithm to apply to the patient sensor data, and the second security policy indicating no encryption algorithm for the device usage data, and an access level datum identifying first and second access levels for the first and second data consuming devices respectively, the first access level allowing access to the patient sensor data, and the second access level, different from the first access level, preventing access to the patient sensor data, and a medical device datum identifying a data format and communication protocol used by the medical device; and a transceiver configured to communicate with the first and second data consuming devices, wherein the processor is configured to communicate the patient sensor data and the device usage data associated with the medical device to the first and second data consuming devices respectively, in accordance with the profile datums, and wherein responsive to the edge communication device being moved from a first network to a second network, the edge communication device is configured to receive at least a portion of a second profile stored on a second edge communication device associated with another medical device on the second network, and adjust the profile datums stored in the edge communication device based on the at least a portion of the second profile.

18. The edge communication device of claim 17, further comprising an antenna and a plurality of connectivity adapters operable with the antenna to communicate with the first data consuming device, and the profile configures the edge communication device to select two or more connectivity adapters of the plurality of connectivity adapters to enable data communication with the first data consuming device, each of the two or more connectivity adapters being enabled to simultaneously communicate with the first data consuming device using the antenna.

19. The edge communication device of claim 18, wherein the two or more connectivity adapters are enabled to simultaneously communicate a same set of patient sensor data to the first data consuming device.

20. The edge communication device of claim 17, wherein the edge communication device is further configured to reformat data from the medical device into first and second data formats expected by the first and second data consuming devices respectively.

* * * * *